(12) United States Patent  
Baharav et al.

(10) Patent No.: US 6,972,714 B1  
(45) Date of Patent: Dec. 6, 2005

(54) OPTICALLY-AUGMENTED MICROWAVE IMAGING SYSTEM AND METHOD

(75) Inventors: Izhak Baharav, San Jose, CA (US); Robert C. Taber, Palo Alto, CA (US); S. Jeffrey Rosner, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/863,733

(22) Filed: Jun. 8, 2004

(51) Int. Cl.[7] .............................................. G01S 13/89
(52) U.S. Cl. ...................... 342/179; 342/22; 342/27; 342/52; 342/53; 342/54; 342/55; 342/175; 342/176; 342/195; 342/196
(58) Field of Search ..................... 342/22, 25 R–25 F, 342/27, 28, 52–59, 82–103, 175, 176, 179, 342/180, 190–196; 382/113; 345/619

(56) References Cited

U.S. PATENT DOCUMENTS

| | | | |
|---|---|---|---|
| 4,831,383 A * | 5/1989 | Ohnishi et al. ................ 342/22 |
| 4,984,279 A * | 1/1991 | Kidney et al. ................ 382/113 |
| 5,081,456 A * | 1/1992 | Michiguchi et al. ........... 342/22 |
| 5,083,089 A | 1/1992 | Yukl | |
| 5,365,237 A | 11/1994 | Johnson et al. | |
| 5,444,441 A * | 8/1995 | Sutton ........................ 342/22 |
| 5,774,088 A * | 6/1998 | Kreithen ....................... 342/22 |
| 5,835,054 A * | 11/1998 | Warhus et al. ................. 342/22 |
| 5,982,326 A | 11/1999 | Chow et al. | |
| 6,037,908 A | 3/2000 | Phillips et al. | |
| 6,057,761 A | 5/2000 | Yukl | |
| 6,061,068 A * | 5/2000 | Hoffman et al. ............. 345/619 |
| 6,501,414 B2 | 12/2002 | Arndt et al. | |
| 6,545,945 B2 * | 4/2003 | Caulfield ...................... 342/22 |
| 6,720,905 B2 * | 4/2004 | Levitan et al. ................ 342/22 |

* cited by examiner

*Primary Examiner*—Bernarr E. Gregory

(57) ABSTRACT

An imaging system includes an optical (visible-light or near IR) imaging system and a microwave imaging system. The optical imaging system captures an optical image of the object, produces optical image data representing the optical image and extracts optical image information from the optical image data. The microwave imaging system produces microwave image data representing a microwave image of the object in response to the optical image information.

16 Claims, 5 Drawing Sheets

OPTICALLY-AUGMENTED MICROWAVE IMAGING SYSTEM AND METHOD

BACKGROUND OF THE INVENTION

A typical microwave imaging system operates in the frequency range of 1 GHz to 100 GHz, corresponding to wavelengths in free-space of 30 cm to 0.33 cm. By comparison, optical or visible light imaging systems operate in the frequency range of 750 THz to 430 THz, corresponding to wavelengths of 0.4 µm to 0.7 µm. Though both are electromagnetic waves in nature, the different wavelengths produce different imaging characteristics. For example, microwave radiation is capable of penetrating objects that are opaque to visible light. As a result, microwave imaging systems are able to obtain measurements of the object beyond the external layer.

Traditional microwave imaging systems rely on measuring the microwave radiation from an object, and constructing an image of the object based on the radiation measurements. The radiation measurement is obtained using an antenna and adjacent receiver circuitry. The antenna can be a single element antenna, or one that is composed of an array of smaller sub-antenna elements. In addition, the antenna and the receiver circuitry can operate in a transmitting mode, a receiving mode or a combination of transmitting and receiving modes.

The measured microwave radiation includes either one or both of the amplitude and the phase of the wavefront scattered from the object. The amplitude and/or phase measurements are processed to construct an image of the object. For example, the sampled wavefront can be constructed using a Fourier-based computer image construction algorithm. An example of a Fourier-based computer image construction algorithm is described in *Fourier Array Imaging* by Mehrdad Soumekh (1994). However, the construction process is often computationally intensive. In addition, in many instances, the resulting constructed image suffers from poor resolution or processing artifacts, such as speckles. Therefore, what is needed is a microwave imaging system for constructing a high quality image with reduced computational complexity.

SUMMARY OF THE INVENTION

Embodiments of the present invention provide an imaging system including an optical (visible light or near IR) imaging system and a microwave imaging system. The optical imaging system is configured to capture an optical image of the object, produce optical image data representing the optical image and extract optical image information from the optical image data. The microwave imaging system is operable to illuminate the object with microwave radiation and to make microwave measurements in response thereto. The microwave imaging system is configured to produce microwave image data representing a microwave image of the object in response to the optical image information and the microwave measurements.

In one embodiment, the microwave imaging system is operable to identify data points corresponding to spatial regions associated with the object in response to the optical image information, and solve for the identified data points using the microwave measurements. In a further embodiment, the microwave imaging system is operable to direct microwave illumination to the spatial regions associated with the object. The spatial regions are identified using the optical image information. In another embodiment, the microwave imaging system is operable to track motion of the object in response to the optical image information.

The optical imaging system uses a fast and simple algorithms to extract the optical image information. The optical image information can reduce the computational complexity of constructing the microwave image and limit the microwave illumination to the regions of interest on the object, thereby enabling improved resolution and a reduction in artifacts of the microwave image. Furthermore, the invention provides embodiments with other features and advantages in addition to or in lieu of those discussed above. Many of these features and advantages are apparent from the description below with reference to the following drawings.

BRIEF DESCRIPTION OF THE DRAWINGS

The disclosed invention will be described with reference to the accompanying drawings, which show important sample embodiments of the invention and which are incorporated in the specification hereof by reference, wherein.

DETAILED DESCRIPTION OF THE EXEMPLARY EMBODIMENTS

Figure 1:
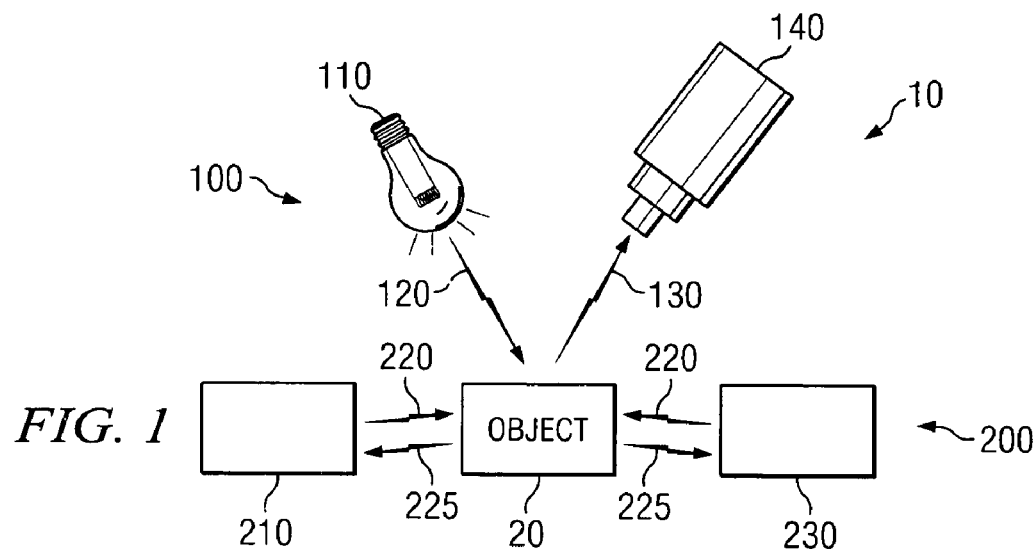
FIG. 1 is a simplified representation of an exemplary imaging system incorporating an optical (visible-light) imaging system with a microwave imaging system, in accordance with embodiments of the present invention.

FIG. 1 is a simplified representation of an exemplary imaging system 10 in which a microwave imaging system 200 is augmented with an optical imaging system 100. As used herein, the term "microwave imaging system" refers to an imaging system operating the microwave frequency range, and the resulting images obtained by the microwave imaging system are referred to as "microwave images." In addition, as used herein, the term "optical imaging system" refers to an imaging system operating in the visible light or near IR frequency range, and the resulting images obtained by the optical imaging system are referred to as "optical images" in order to differentiate these images from microwave images obtained by the microwave imaging system.

The imaging system 10 can be used, for example, in airport security systems for inspecting luggage or passengers, or any other microwave imaging application. The optical imaging system 100 includes a light source 110 for illuminating an object 20 with light 120 and a camera 140 for receiving reflected light 130 from the object to capture an optical image of the object 20. The camera 140 includes one or more cameras 140 for capturing the optical image. The microwave imaging system 200 includes microwave nodes 210 and 230 configured to emit microwave radiation 220 for illuminating the object 20. Microwave nodes 210 and 230 are further configured to receive reflected microwave radiation 225 from the object to capture a microwave image of the object 20.

Figure 2:
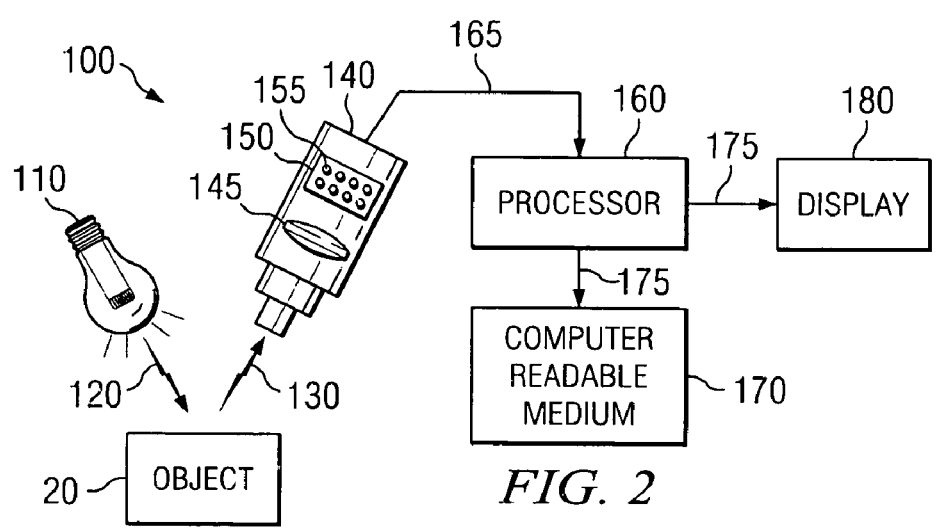
FIG. 2 is a simplified representation of an exemplary optical imaging system, in accordance with embodiments of the present invention.

The optical imaging system 100 is shown in more detail in FIG. 2. As described above, the light source 110 illuminates the object 20 with light 120. The light source 110 can be any suitable source of visible or near IR light. For example, the light source 110 can include one or more light emitting elements, such as one or more point light sources, one or more collimated or structured light sources, one or more arrays of light sources, or any other combination of light sources suitable for use in the optical imaging system 100. Reflected light 130 from the object 20 is received by the camera 140. It should be understood that the camera 140 includes one or more cameras optimally positioned in the optical imaging system 100. For each camera 140, the reflected light 130 is directed by a lens 145 to a sensor 150 within the camera 140. The sensor 140 includes a plurality of pixels 155 for capturing the optical image of the object 20 and producing optical image data 165 representing the optical image.

The optical imaging system 100 further includes a processor 160 for receiving the optical image data 165 representing the image of the object 20 and processing the optical image data 165 to extract optical image information 175 associated with the optical image. The processor 160 can be a microprocessor, microcontroller, programmable logic device or other type of processing device capable of performing the functions described herein. In addition, the processor 160 can include multiple processors or be a single general-purpose processor capable of executing a number of algorithms.

The optical image information 175 is used by the microwave imaging system 200 (shown in FIG. 1) to produce microwave image data representing the microwave image of the object 20. For example, in one embodiment, the optical image information 175 identifies data points corresponding to spatial regions of interest associated with the object 20. The identified data points corresponding to the spatial regions of interest can be used to direct microwave radiation to the spatial regions of interest or to construct the microwave image using the microwave measurements corresponding to the identified data points. In another embodiment, the optical image information 175 is used to track motion of the object 20 by correlating the microwave measurements with a position of the object 20.

The optical image information 175 can be stored in a computer-readable medium 170 for later processing by the microwave imaging system and/or output directly to display 180. The computer-readable medium 170 can be a memory device, such as random access memory (RAM), read-only memory (ROM), flash memory, EEPROM, disk drive, compact disk, floppy disk or tape drive, or any other type of storage device. Additional processing information (not shown) can also be stored on the computer-readable medium 170 and accessed by the processor 160. For example, such processing information can include various processing parameters, such as algorithms that can be used to process the image data 165 and extract the optical image information 175 from the image data 165.

Figure 3:
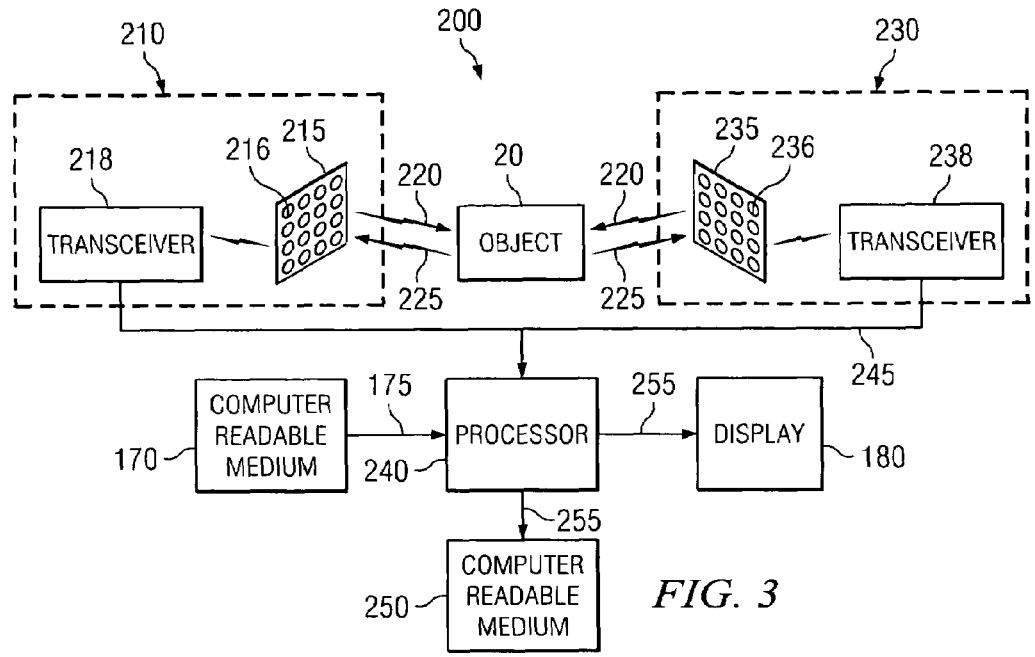
FIG. 3 is a simplified representation of an exemplary microwave imaging system, in accordance with embodiments of the present invention.

The microwave imaging system 200 is shown in more detail in FIG. 3. As described above in connection with FIG. 1, the microwave nodes 210 and 230 illuminate the object 20 with microwave radiation 220 and receive reflected microwave radiation 225 from the object 20 to capture a microwave image of the object 20. Microwave nodes 210 and 220 each include a respective antenna array 215 and 235 having multiple antenna elements 216 and 235, respectively. Antenna elements 216 and 236 direct microwave radiation 220 towards the object 20 and receive reflected microwave radiation 225 from the object 20.

It should be understood that one or more microwave nodes 210 and 220 can be used, depending on the type of microwave node 210 and 220 and the application. It should further be understood that microwave nodes 210 and 220 can include any type of microwave antenna, including point source antennas, unidirectional antennas that receive microwave radiation from the object and bi-directional antennas that both transmit microwave radiation 220 towards the object 20 and receive reflected microwave radiation 225 from the object 20. For example, the microwave nodes 210 and 230 can include separate transmit and receive antennas, separate transmit and receive antenna elements within the same antenna array, separate transmit and receive antenna arrays or one or more antennas or antenna elements capable of both transmitting and receiving microwave radiation.

Antenna elements 216 and 236 are controlled by respective transceivers 218 and 238. For example, transceivers 218 and 238 control the antenna elements 216 and 236, respectively, to direct the microwave radiation 220 to regions of interest associated with the object 20 (e.g., on or around the object). Transceivers 218 and 238 further monitor the received reflected microwave radiation 225, measure the intensity and/or the phase of the reflected microwave radiation 225 as a function of the direction of the received microwave radiation 225 and record microwave measurements 245 corresponding to a characteristic of the response of the object 20 to the microwave radiation 220.

In one embodiment, the microwave measurements 245 include amplitude and phase measurements of the wavefront scattered from the object 20. The measurements 245 are transmitted to processor 240 which operates to construct a microwave image of the object 20 in response to the measurements 245. For example, the processor 240 can construct the microwave image using a Fourier-based construction algorithm. The processor 240 can be a microprocessor, microcontroller, programmable logic device or other type of processing device capable of performing the functions described herein. In addition, the processor 240 can include multiple processors or be a single general-purpose processor capable of executing a number of algorithms.

The measurements 245 are used by the processor 240 to produce microwave image data 255 representing the microwave image of the object 20. The microwave image data 255 can be stored in a computer-readable medium 250 for later processing by the microwave imaging system 200 and/or output directly to display 180. The computer-readable medium 250 can be a memory device, such as random access memory (RAM), read-only memory (ROM), flash memory, EEPROM, disk drive, compact disk, floppy disk or tape drive, or any other type of storage device. Additional processing information (not shown) can also be stored on the computer-readable medium 250 and accessed by the processor 240. For example, such processing information can include various processing parameters, such as algorithms that can be used to process the measurements 245 and produce the microwave image data 255.

The processor 240 further receives the optical image information 175 from the computer-readable medium 170 that stored the optical image information 175 for the optical imaging system 100 (shown in FIG. 2). The computer-readable medium 170 can be the same computer-readable medium 250 used by the microwave imaging system 200 or a separate computer-readable medium. The processor 240 uses the optical image information 175 in producing the microwave image data 255. For example, as discussed above, in one embodiment, the optical image information 175 identifies data points corresponding to spatial regions of interest associated with the object 20. The processor 240 uses the optical image information 175 to control transceivers 218 and 238 to direct the microwave radiation 220 to the spatial regions of interest or to construct the microwave image using the measurements 245 corresponding to the identified data points. In another embodiment, the processor 240 uses the optical image information 175 to track motion of the object 20 by correlating the received microwave measurements 245 with a position of the object 20, as identified by the optical image information 175.

Figure 4:
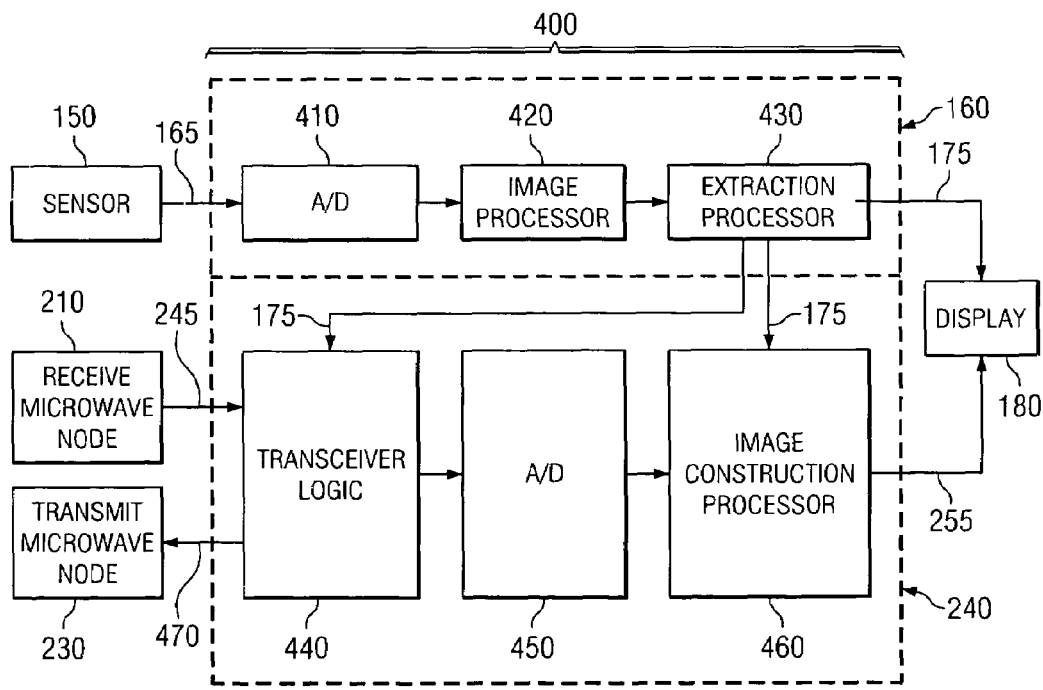
FIG. 4 is a block diagram of an image processing system for augmenting a microwave imaging system with an optical imaging system, in accordance with embodiments of the present invention.

FIG. 4 is a block diagram of an image processing system 400 in which a microwave imaging system is augmented with an optical imaging system, in accordance with embodiments of the present invention. The image processing system 400 includes optical image processor 160 and microwave image processor 240. The optical image processor 160 includes image processor 420 and extraction processor 430. In one embodiment, image processor 420 and extraction processor 430 are ASICs or FPGA circuits configured to perform the functions described below. In another embodiment, image processor 420 and extraction processor 430 are combined in a general-purpose processor that executes algorithms to perform the functions described below.

The optical image processor 160 receives from sensor 150 image data 165 representing an optical image. It should be understood that if there are multiple cameras, each camera provides a separate optical image to the optical image processor 160. In addition, depending on the light source used, the optical image processor 160 may further need to obtain information concerning the illumination pattern of the light source.

The image data 165 is converted from analog to digital by A/D converter 410 and passed to image processor 420 that processes the digital image data 165. For example, if the sensor 150 is a color sensor incorporating a color filter array, the image processor 420 can demosaic the image. Demosaicing is a process by which missing color values for each pixel location are interpolated from neighboring pixels. There are a number of demosaicing methods known in the art today. By way of example, but not limitation, various demosaicing methods include pixel replication, bilinear interpolation and median interpolation. Other types of processing that the image processor 240 can perform include noise filtering and image enhancement.

Extraction processor 430 is connected to receive the processed image data from image processor 420, and operates to extract the optical image information 175 from the processed image data. There are a number of fast and simple known algorithms that can be used to extract the optical image information 175 from the image data 165. For example, in one embodiment, extraction processor 430 extracts the 3D surface of an object using an image construction algorithm for three-dimensional images. An example of an image construction process for three-dimensional images is described in co-pending and commonly assigned U.S. Application for Patent, Ser. No. 10/392,758, filed Mar. 20, 2003, in which an illumination gradient is used to spatially vary the intensity and/or spectral characteristics of the reflected illumination from the object in order to determine surface gradients at spatial locations on the surface of the object. The surface gradients are then used to construct a three-dimensional image of the object. Other three-dimensional image construction processes include laser triangulation, stereoscopic imaging, structured light and photometric stereo. For example, various three-dimensional image construction processes are described in Horn et al., "Toward Optimal Structured Light Patterns," IEEE Proceedings International Conference on Recent Advances in 3-D Digital Imaging and Modeling, Ottowa, Ontario, Canada, May 12–15, 1997, pp. 28–35 and Beraldin et al., "Optimized Position Sensors for Flying-Spot Active Triangulation System," IEEE Proceedings International Conference on Recent Advances in 3-D Digital Imaging and Modeling, Banff, Albertta, Canada, Oct. 6–10, 2003, pp. 29–36.

In another embodiment, extraction processor 430 extracts features of the object 20 that are of interest. It should be understood that as used herein, the phrase "features of the object" includes measurements of the object 20, components on a surface of or within the object 20 or other indicia of the object 20. In further embodiments, extraction processor 430 extracts any other information from the image data 165 that is desired.

The optical image information 175 is output by the extraction processor 430 to the microwave processor 240 for use in constructing the microwave image. The optical image information 175 is also transmitted from the extraction processor 430 to the display 180.

Microwave processor 240 includes transceiver logic 440, A/D converter 450 and image construction processor 460. In one embodiment, transceiver logic 440 and image construction processor 460 are ASICs or FPGA circuits configured to perform the functions described below. In another embodiment, transceiver logic 440 and image construction processor 460 are combined in a general-purpose processor that executes algorithms to perform the functions described below.

The transceiver logic 440 receives microwave measurements 245 including amplitude and phase measurements of the scattered wavefront from a receive microwave node (e.g., node 210). It should be understood that the receive microwave node 210 can include a single antenna, an entire antenna array or one or more antenna elements within one or more antenna arrays. The microwave measurements 165 are converted from analog to digital by A/D converter 450 and passed to image construction processor 460 to construct a microwave image of the object. The image construction processor 460 produces microwave image data 255 representing the microwave image of the object and transmits the microwave image data 255 to the display 180.

The optical image information 175 output by the extraction processor 430 is received at either one or both of the transceiver logic 440 and the image construction processor 460. In one embodiment, the optical image information 175 identifies data points corresponding to spatial regions of interest associated with the object 20. In one implementation embodiment, the transceiver logic 440 uses the optical image information 175 to provide transmit instructions 470 to the transmit microwave node (e.g., microwave node 230) to direct the microwave radiation 220 to the spatial regions (or regions) of interest. It should be understood that the transmit microwave node 230 can include a single antenna, an entire antenna array or one or more antenna elements within one or more antenna arrays. In another implementation embodiment, the image construction processor 460 uses the optical image information 175 to construct the microwave image using the measurements 245 corresponding to the identified data points.

For example, a conventional microwave image construction process is described in David M. Sheen et al., "Three-dimensional Millimeter-Wave Imaging for Concealed Weapon Detection," IEEE Tran. On Microwave Theory and Techniques (MTT), Vol.49 (9): 1581–1592, September 2001 (hereinafter "Sheen"). In the Sheen paper, the whole volume (x,y,z) is discretely sampled in the solution. A 3D inverse Fourier transform is done on the whole volume, which introduces a significant computational load and possible inaccuracies that can manifest themselves as noise. With the optical image information 175, the actual volume occupied by the object being interrogated can be identified to determine what data points in the volume really need to be solved for. Thus, in the discrete-sampling of the space, only relevant data points need to be addressed. Depending on the maximum allowed volume to analyze, and the minimum that can be encountered, the computational load can be significantly reduced.

As an example, if the object is 1 m (width)×2 m (long)×1 m (deep), the volume of the object is 1×1×2=2 m$^3$. However, since the orientation is typically not known, a volume of 1.4×1.4×2=4 m$^3$ may need to be solved for in a conventional microwave image construction.

By using the optical image information 175 to determine the actual volume occupied by the object, the image construction processor 460 only needs to solve for the actual volume, which represents a large saving in computation time. This saving in complexity can be translated into one or more of: (1) faster computation, (2) fewer measurements by the system (e.g., fewer frequencies used or fewer antennas/receivers), and (3) better accuracy or rejection of aliasing "images" of the object that fall outside of the properly-defined region of interest. Additionally, the optical image information 175 can provide knowledge about the shadows induced by the object 20. Determining which data points are shadowed will produce a "cleaner" solution with reduced artifacts in the microwave image and/or a faster solution.

In another embodiment, the optical image information 175 includes 3D object position information that is used by the image construction processor 240 to determine the location of the object in three dimensions while in motion by correlating the received microwave measurements 245 with the optical image information 175. The optical processor 160 can correlate every point at a given time with the corresponding point at a previous time through the use of conventional visible-light tracking algorithms. This enables the microwave processor 240 to solve for the microwave image data 255, even when the object has moved. Examples of tracking algorithms are described in Shirai, "Estimation of 3-D Pose and Shape from a Monocular Image Sequence and Real-Time Human Tracking," IEEE Proceedings International Conference on Recent Advances in 3-D Digital Imaging and Modeling, Oftowa, Ontario, Canada, May 12–15, 1997, pp. 130–139, and Mecke et al., "3-D Motion and Shape from Multiple Image Sequences," IEEE Proceedings International Conference on Recent Advances in 3-D Digital Imaging and Modeling, Banff, Alberta, Canada, Oct. 6–10, 2003, pp. 155–162.

Figure 5A:
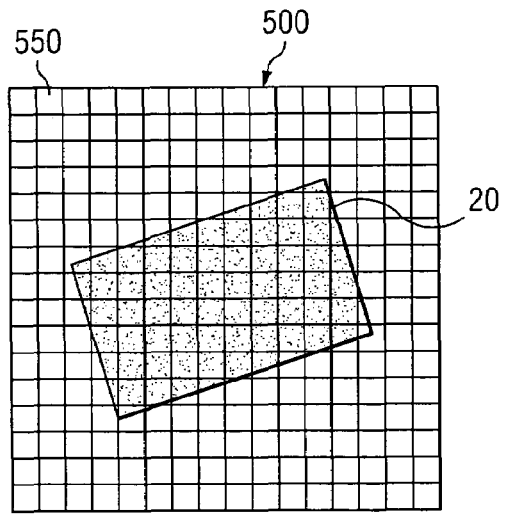
FIG. 5A illustrates a simplified prior art image construction of a volume of an object.
Figure 5B:
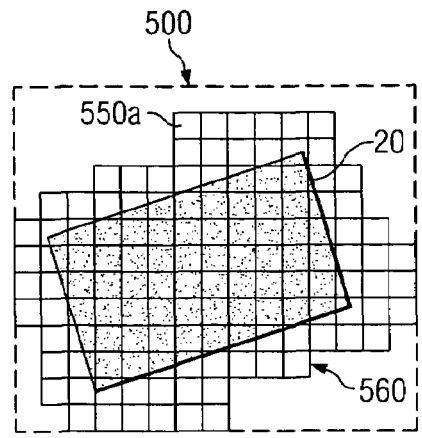
FIG. 5B illustrates a simplified image construction of a volume of an object, in accordance with one embodiment of the present invention.

FIGS. 5A and 5B illustrate a simplified image construction of a volume of an object 20. FIG. 5A represents a conventional image construction, while FIG. 5B represents an image construction in accordance with one embodiment of the present invention. FIGS. 5A and 5B both illustrate a two-dimensional example that can be readily applied to three dimensions.

In FIG. 5A, a grid 500 made up of multiple data points 550 is used to solve for the whole area. Since the orientation/location of the object 20 in space is unknown, the grid must accommodate all variations. Therefore, in FIG. 5A, each of the data points 550 in the grid 500 is solved for. By contrast, as shown in FIG. 5B, when the location of the object 20 is known (at least approximately), only a subset 560 of the data points 550a needs to be solved for.

Figure 6:
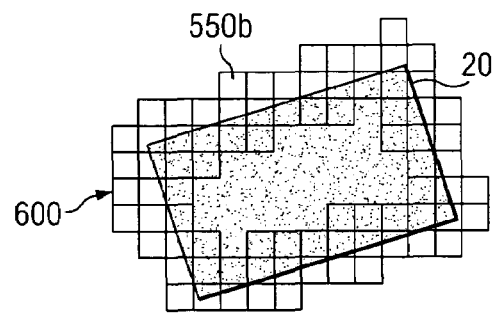
FIG. 6 illustrates a simplified construction of a perimeter of an object, in accordance with another embodiment of the present invention.

FIG. 6 illustrates a simplified construction of the perimeter of an object 20, in accordance with another embodiment of the present invention. FIG. 6 also illustrates a two-dimensional example that can be readily applied to three dimensions. FIG. 6 uses the same grid 500 shown in FIG. 5A. However, in FIG. 6, only the data points 550b corresponding to a perimeter 600 of the object 20 are solved for. The perimeter 600 is identified from the optical image information. With certain kinds of objects (e.g., people with loose clothing), the perimeter 600 can include data points within a "deep" shell around the object perimeter, as shown in FIG. 6. In a further embodiment, rather than solving for the whole perimeter, techniques similar to beam-forming can be used to direct microwave radiation to only specific data points in question. The specific data points are identified using the optical image information.

Figure 7A:
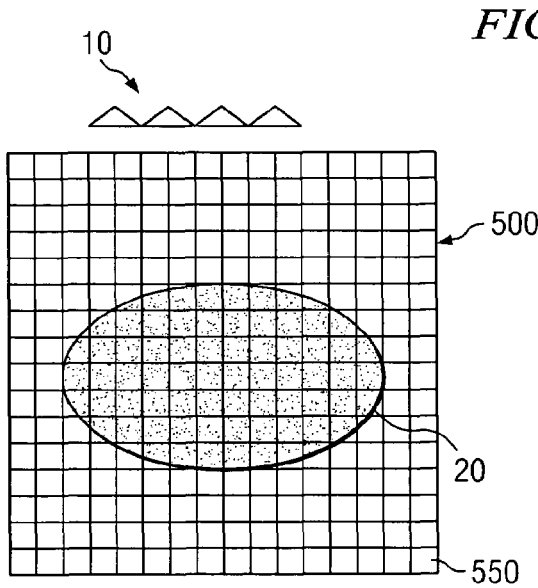
FIG. 7A illustrates a simplified prior art image construction of a portion of a perimeter of an object.
Figure 7B:
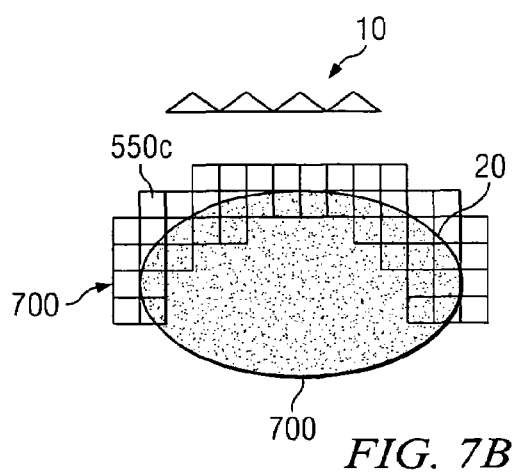
FIG. 7B illustrates a simplified image construction of a portion of a perimeter of an object, in accordance with another embodiment of the present invention.

FIGS. 7A and 7B illustrate a simplified image construction of a portion of a perimeter of an object 20. FIG. 7A represents a conventional image construction, while FIG. 7B represents an image construction in accordance with another embodiment of the present invention. The advantages of the above perimeter method are amplified by the fact the human body is a very good reflector in the microwave frequency range. Thus, for example, in FIGS. 7A and 7B, the ellipse represents a cross section of a human body (object 20), and the triangles represent the imaging system 10. Traditionally, the whole volume would be solved for, even though due to the reflectivity of the body, only the portion of the body facing imaging system 10 is imaged. In accordance with embodiments of the present invention, using the microwave imaging system augmented with an optical imaging system, a boundary region 700 including data points 550c corresponding to a portion of a perimeter of the human body is identified using the optical image information. The microwave imaging system then directs microwave radiation to and solves only for the data points 550c in the boundary region 700.

Figure 8:
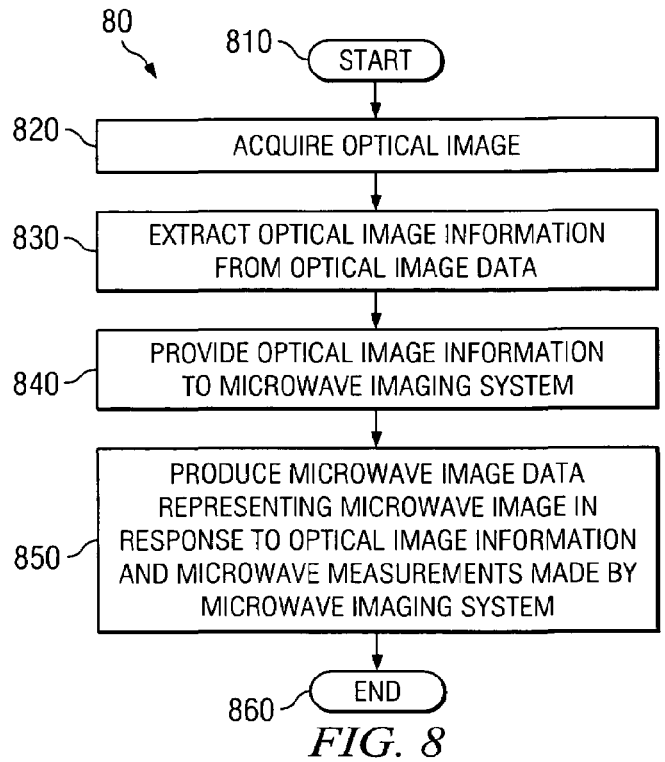
FIG. 8 is a flow chart illustrating an exemplary process for determining a microwave image by augmenting a microwave imaging system with an optical imaging system, in accordance with embodiments of the present invention.

FIG. 8 is a flow chart illustrating an exemplary process 800 for producing microwave image data representing a microwave image using an optically-augmented microwave imaging system, in accordance with embodiments of the present invention. The process begins at block 810. At block 820, an optical image of the object is acquired by the optical imaging system. At block 830, optical image information is extracted from the optical image data representing the optical image, and at block 840, the optical image information is provided to the microwave imaging system. At block 850, the microwave imaging system produces microwave image data representing the microwave image in response to the optical image information and microwave measurements made by the microwave imaging system. The process ends at block 860.

Figure 9:
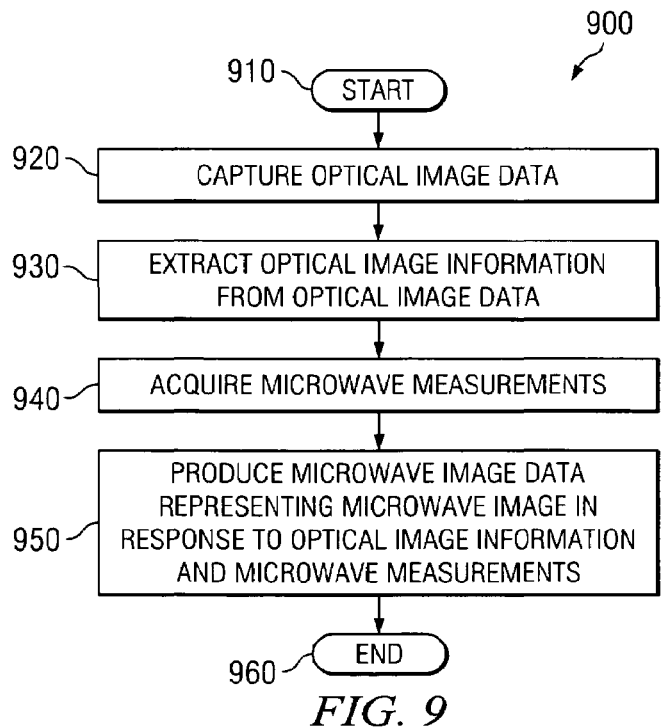
FIG. 9 is a flow chart illustrating an exemplary process for constructing a microwave image using optical image information provided by the optical imaging system, in accordance with one embodiment of the present invention.

FIG. 9 is a flow chart illustrating an exemplary process 900 for constructing a microwave image in response to optical image information provided by the optical imaging system, in accordance with one embodiment of the present invention. The process begins at block 910. At block 920, an optical image of the object is captured by the optical imaging system. At block 930, optical image data representing the optical image is processed to extract optical image information. At block 940, microwave measurements corresponding to various characteristics of the response of the object to microwave radiation are acquired by the microwave imaging system. At block 950, the microwave imaging system produces microwave image data representing the microwave image of the object in response to the optical image information and the microwave measurements. The process ends at block 960.

Figure 10:
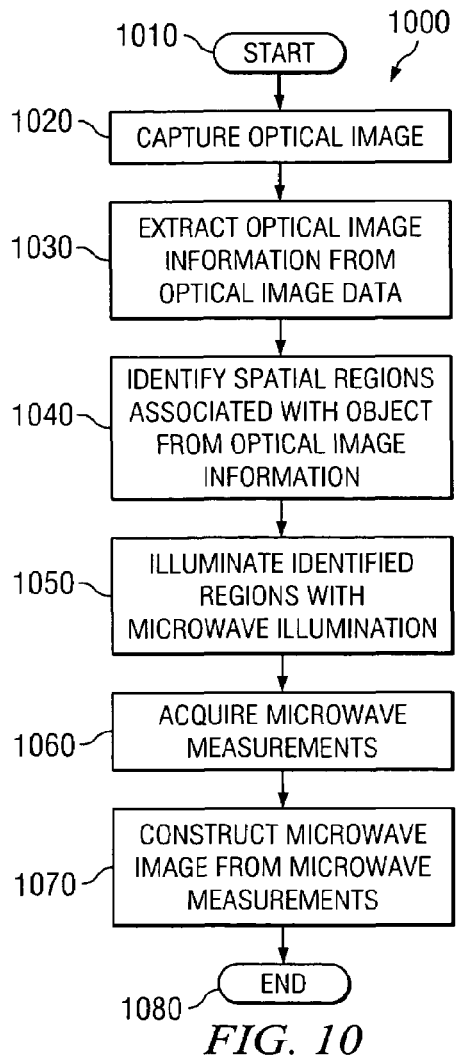
FIG. 10 is a flow chart illustrating an exemplary process for directing microwave illumination to regions of interest on an object using optical image information provided by the optical imaging system, in accordance with another embodiment of the present invention.

FIG. 10 is a flow chart illustrating an exemplary process 1000 for directing microwave illumination to regions of interest on an object in response to optical image information provided by the optical imaging system, in accordance with another embodiment of the present invention. The process begins at block 1010. At block 1020, an optical image of the object is captured by the optical imaging system. At block 1030, optical image data representing the optical image is processed to extract optical image information. At block 1040, spatial regions (e.g., regions of interest) associated with the object are identified using the optical image information. At block 1050, the identified spatial regions or regions of interest are illuminated with microwave radiation, and at block 1060, microwave measurements corresponding to various characteristics of the response of the object to the microwave radiation are acquired by the microwave imaging system. At block 1070, the microwave imaging system constructs the microwave image of the object from the microwave measurements by producing microwave image data representing the microwave image. The process ends at block 1080.

Figure 11:
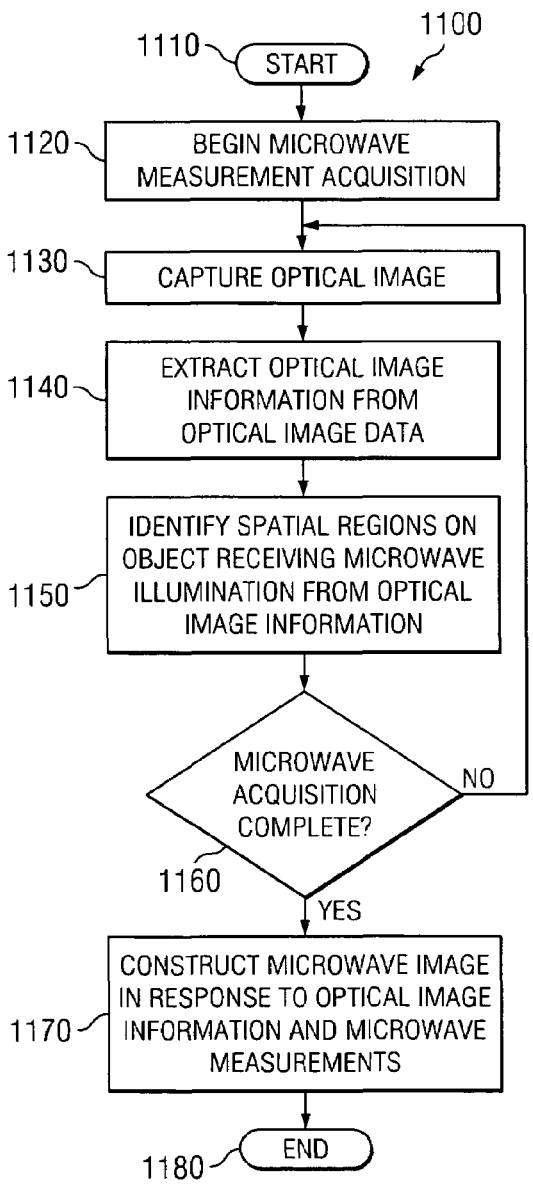
FIG. 11 is a flow chart illustrating an exemplary process for tracking motion of the object using optical image information provided by the optical imaging system to construct a microwave image of the object.

FIG. 11 is a flow chart illustrating an exemplary process 1100 for tracking motion of the object using optical image information provided by the optical imaging system to construct a microwave image of the object. The process begins at block 1110. At block 1120, the microwave imaging system begins to acquire microwave measurements corresponding to various characteristics of the response of the object to microwave radiation. At block 1130, an optical image of the object is captured by the optical imaging system. At block 1140, optical image data representing the optical image is processed to extract optical image information. At block 1150, the optical image information is used to determine the location of the object and the spatial regions on the object that were illuminated by microwave radiation. At block 1160, a determination is made whether the microwave measurement acquisition process is complete. If not, an additional optical image of the object is captured at block 1130 and is processed in blocks 1140–1150 to determine a new location of the object that is correlated with the microwave measurements. If the microwave acquisition process is complete, at block 1170, the microwave imaging system constructs the microwave image of the object in response to the optical image information and the microwave measurements. The process ends at block 1180.

The innovative concepts described in the present application can be modified and varied over a wide rage of applications. Accordingly, the scope of patents subject matter should not be limited to any of the specific exemplary teachings discussed, but is instead defined by the following claims.

What is claimed is:

1. An imaging system, comprising:
   an optical imaging system configured to capture an optical image of an object, to produce optical image data representing the optical image and to extract optical image information from the optical image data; and
   a microwave imaging system operable to illuminate the object with microwave radiation and to make microwave measurements in response thereto, said microwave imaging system being configured to produce microwave image data representing a microwave image of the object in response to the optical image information and the microwave measurements.

2. The imaging system of claim 1, wherein the microwave measurements measure a characteristic of the response of the object to the microwave radiation.

3. The imaging system of claim 1, wherein said microwave imaging system is operable in response to the optical image information to identify data points corresponding to spatial regions associated with the object, said microwave imaging system being further operable to solve for the identified data points using the microwave measurements to produce the microwave image data.

4. The imaging system of claim 3, wherein said microwave imaging system is operable to direct microwave radiation to the spatial regions in response to the optical image information.

5. The imaging system of claim 3, wherein the spatial regions are located at the perimeter of the object.

6. The imaging system of claim 3, wherein the spatial regions are located within a boundary region including at least one side of the object.

7. The imaging system of claim 3, wherein the spatial regions enable said microwave imaging system to solve for the data points in a volume occupied by the object.

8. The imaging system of claim 1, wherein said microwave imaging system is operable to track motion of the object in response to the optical image information.

9. The imaging system of claim 1, wherein said optical imaging system comprises:
   a light source arranged to illuminate the object; and
   a sensor for producing the optical image data in response to light reflected by the object.

10. The imaging system of claim 1, wherein said microwave imaging system comprises:
   a microwave node configured to direct microwave radiation towards the object and receive reflected microwave radiation from the object.

11. A method for imaging an object, the method comprising:
- acquiring optical image data representing an optical image of an object;
- extracting optical image information from the optical image data; and
- producing microwave image data representing a microwave image of the object in response to the optical image information and microwave measurements taken responsive to illumination of the object with microwave radiation.

12. The method of claim 11, wherein said producing further comprises:
- using the optical image information to identify data points corresponding to spatial regions associated with the object; and
- solving for the identified data points using the microwave measurements.

13. The method of claim 12, further comprising:
- directing the microwave radiation to the spatial regions using the optical image information.

14. The method of claim 11, wherein said producing further comprises:
- tracking motion of the object in response to the optical image information to produce the microwave image data.

15. The method of claim 11, wherein said acquiring further comprises:
- illuminating the object with light;
- receiving light reflected from the object; and
- producing the optical image data in response to the reflected light.

16. The method of claim 11, wherein said producing further comprises:
- illuminating the object with microwave radiation; and
- receiving microwave radiation reflected by the object.

* * * * *

UNITED STATES PATENT AND TRADEMARK OFFICE
CERTIFICATE OF CORRECTION

PATENT NO. : 6,972,714 B1
DATED : December 6, 2005
INVENTOR(S) : Baharav et al.

It is certified that error appears in the above-identified patent and that said Letters Patent is hereby corrected as shown below:

<u>Title page,</u>
Item [75], Inventors, delete "San Jose," and insert -- Palo Alto, --.

Signed and Sealed this

Twenty-third Day of May, 2006

JON W. DUDAS
*Director of the United States Patent and Trademark Office*